United States Patent
Hashmi et al.

(10) Patent No.: US 10,676,420 B2
(45) Date of Patent: Jun. 9, 2020

(54) PROCESS FOR PRODUCING TEREPHTHALIC ACID

(71) Applicant: SABIC Global Technologies B.V., Bergen op Zoom (NL)

(72) Inventors: Syed Azhar Hashmi, Riyadh (SA); Labeeb A. Chaudhary, Riyadh (SA); Nedumbamana Sankaran, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 42 days.

(21) Appl. No.: 15/770,227

(22) PCT Filed: Oct. 17, 2016

(86) PCT No.: PCT/IB2016/056227
§ 371 (c)(1),
(2) Date: Apr. 23, 2018

(87) PCT Pub. No.: WO2017/068487
PCT Pub. Date: Apr. 27, 2017

(65) Prior Publication Data
US 2018/0305287 A1 Oct. 25, 2018

Related U.S. Application Data
(60) Provisional application No. 62/245,322, filed on Oct. 23, 2015.

(51) Int. Cl.
*C07C 51/265* (2006.01)
*B01J 23/50* (2006.01)
*B01J 27/08* (2006.01)
*B01J 31/04* (2006.01)

(52) U.S. Cl.
CPC .......... *C07C 51/265* (2013.01); *B01J 23/50* (2013.01); *B01J 27/08* (2013.01); *B01J 31/04* (2013.01); *C07C 2601/16* (2017.05)

(58) Field of Classification Search
CPC ... C07C 51/265; C07C 63/26; C07C 2601/16; B01J 23/50; B01J 27/08; B01J 31/04
See application file for complete search history.

(56) References Cited

U.S. PATENT DOCUMENTS

| | | | | |
|---|---|---|---|---|
| 2,245,528 A | * | 6/1941 | Loder | C07B 35/04 562/417 |
| 3,334,135 A | * | 8/1967 | Ichikawa | C07C 51/265 562/412 |
| 3,626,000 A | * | 12/1971 | Tsunoi | C07C 51/265 562/417 |
| 3,660,476 A | | 5/1972 | Ichikawa et al. | |
| 5,516,423 A | * | 5/1996 | Conoby | B01J 19/0006 137/391 |
| 2009/0326265 A1 | | 12/2009 | Hashmi et al. | |
| 2012/0004450 A1 | * | 1/2012 | Bhattacharyya | C07C 51/265 562/412 |
| 2014/0100386 A1 | | 4/2014 | Bhattacharyya | |

FOREIGN PATENT DOCUMENTS

| | | |
|---|---|---|
| GB | 851562 A | 10/1960 |
| GB | 1220542 A | 1/1971 |
| WO | 2007066365 A1 | 6/2007 |

OTHER PUBLICATIONS

Dong et al. (Hybrid Model of Industrial p-Xylene Oxidation Incorporated Fractional Kinetic Model with Intelligent Models, Ind. Eng. Chem. Res. 52, pp. 2537-2547, Published Jan. 2013) (Year: 2013).*
Jianxin, L. et al. "CO2-Aided Aerial Oxidation of p-Xylene to Terephthalic Acid with Co/Mn/Br Catalyst", Shiyou Huagong/ Petrochemical Technology 38(10):1054-1058—Oct. 2009, 1 page.
International Search Report from the International Searching Authority for International Application No. PCT/IB2016/056227; Date of Completion: Feb. 10, 2017; dated Mar. 1, 2017; 5 Pages.
Written Opinion of the International Searching Authority for International Application No. PCT/IB2016/056227; International Filing Date: Oct. 17, 2016; dated Mar. 1, 2017; 5 Pages.

* cited by examiner

Primary Examiner — Jafar F Parsa
Assistant Examiner — Blaine G Doletski
(74) Attorney, Agent, or Firm — Cantor Colburn LLP

(57) ABSTRACT

A process for producing terephthalic acid, comprising: passing a feed stream through a catalytic reactor wherein the feed stream comprises p-xylene; contacting the feed stream with a catalyst within the catalytic reactor to produce an oxidation reaction wherein the catalyst comprises, less than or equal to 10% of a metal component wherein the metal component comprises cobalt ions, manganese ions, or a combination comprising at least one of the foregoing, less than or equal to 15% bromide ions, and less than or equal to 2% silver ions; and producing a product stream comprising terephthalic acid, wherein the product stream exits the catalytic reactor.

20 Claims, 1 Drawing Sheet

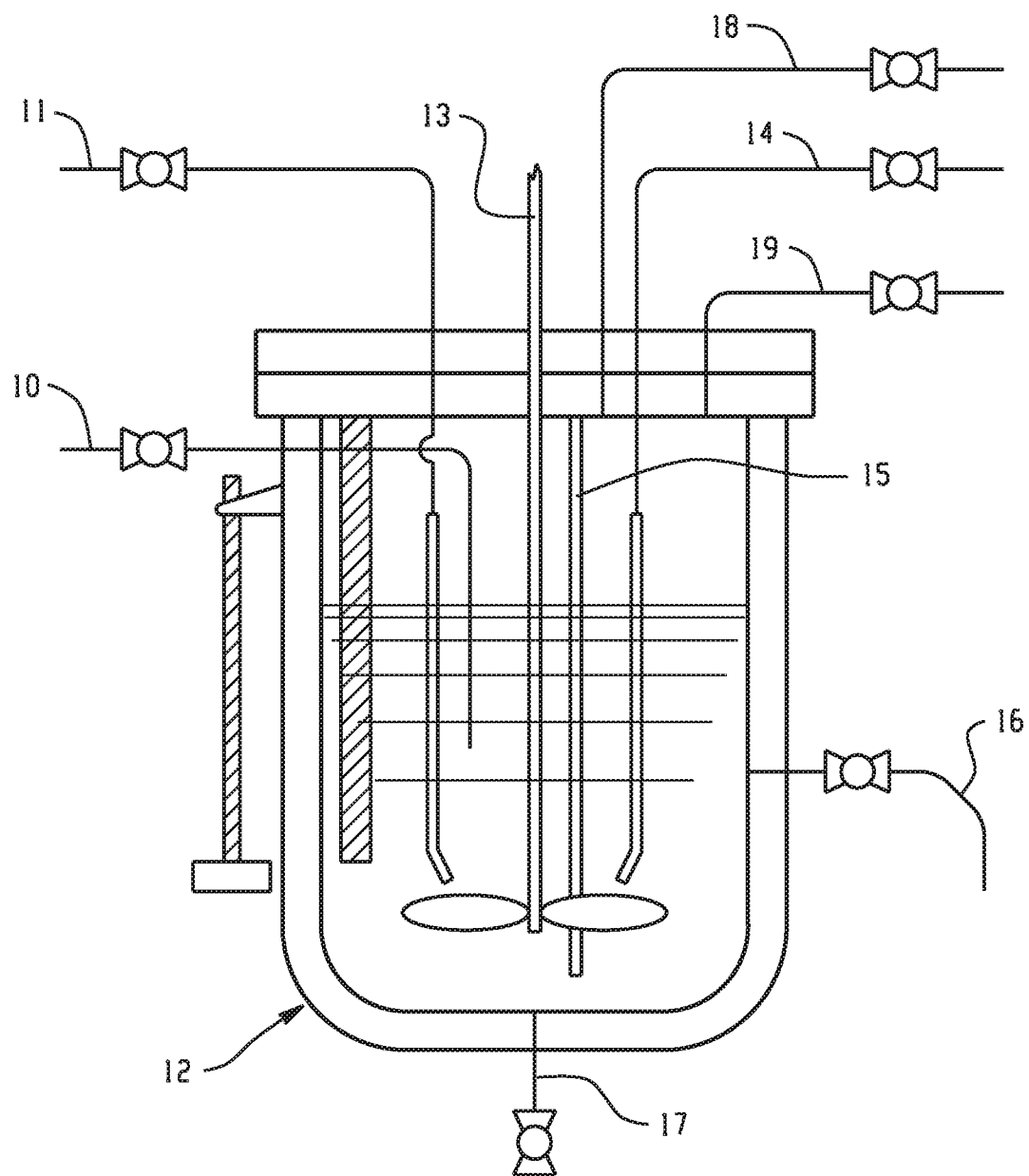

PROCESS FOR PRODUCING TEREPHTHALIC ACID

CROSS REFERENCE TO RELATED APPLICATIONS

This application is a 371 of International Application No. PCT/M2016/056227 filed Oct. 17, 2016, which claims priority to U.S. Application No. 62/245,322, filed Oct. 23, 2015, both of which are incorporated by reference in their entirety herein.

BACKGROUND

Terephthalic acid (TPA) is a highly valuable commercial chemical with a large production capacity. For example, TPA serves a raw material in the production of polyester. Production processes for TPA typically include the liquid phase oxidation of p-xylene with air. The catalyst used is typically a combination of cobalt, manganese, and bromide ions dissolved in acetic acid. Due to the large production capacity of TPA, any improvements to the process with regards to efficiency are very important from an economic point of view. Furthermore, current commercial processes produce harmful impurities. For example, 4-carboxybenzaldehyde (4-CBA) is an impurity that acts as a chain termination agent in subsequent polymerization processes. As a result, the crude TPA produced must undergo a cumbersome and expensive purification process. Therefore, the reduction of 4-CBA levels in the TPA production process is highly significant. In addition, the catalysts used often include highly corrosive acetic acid and bromide ion promoters. These corrosive promoters inconveniently require the use of expensive titanium steel equipment.

Thus, there is a need for a simple and efficient process that can yield valuable TPA with improved catalytic activity, minimal production of harmful impurities, and minimal use of corrosive catalyst promoters.

SUMMARY

Disclosed, in various embodiments, are processes for producing terephthalic acid.

A process for producing terephthalic acid, comprises: passing a feed stream through a catalytic reactor wherein the feed stream comprises p-xylene; contacting the feed stream with a catalyst within the catalytic reactor to produce an oxidation reaction wherein the catalyst comprises, less than or equal to 10% of a metal component wherein the metal component comprises cobalt ions, manganese ions, or a combination comprising at least one of the foregoing, less than or equal to 15% bromide ions, and less than or equal to 2% silver ions; and producing a product stream comprising terephthalic acid, wherein the product stream exits the catalytic reactor.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

The FIGURE is a simplified schematic diagram representing a process for producing terephthalic acid by oxidation of p-xylene in accordance with the present disclosure.

DETAILED DESCRIPTION

Disclosed herein is a process for producing TPA, which can provide a simple and efficient process that can yield valuable TPA with improved catalytic activity, minimal production of harmful impurities, and minimal use of corrosive catalyst promoters. For example, the disclosed process can reduce or eliminate formation of 4-CBA and therefore can eliminate the need for further hydrogenation processes and integrations of additional plant processes. Such a reduction in the formation of 4-CBA during the production of TPA can drastically reduce the production cost of TPA and subsequently, polyester. The disclosed process can improve oxidation efficiency. The disclosed process can also reduce or eliminate the oxidation of acetic acid to carbon monoxide and carbon dioxide. The disclosed process can provide alternatives to the highly corrosive acetic acid and bromide ion promoters which can require the use of expensive titanium steel equipment. The catalyst of the process disclosed herein can provide increased catalytic activity. The process disclosed herein can process a p-xylene feed stream with purity levels of 90% to 95% and still achieve TPA production that reaches the process equipment's maximum capability.

The process disclosed herein can include a feed stream. For example, the feed stream can include p-xylene. For example, the feed stream can include less than or equal to 99 mole percent (mole %) p-xylene. For example, the feed stream can include less than or equal to 90 mole % p-xylene. The feed stream can include o-xylene, m-xylene, p-toluic acid, acetic acid as a solvent, water, catalyst solution, ethyl benzene, or a combination comprising at least one of the foregoing. The feed stream of the present process can be passed through a reactor.

The process disclosed herein can include a reactor. For example, the disclosed process can include a catalytic reactor. The reactor can include a continuous stirred tank, agitator, air stream, drain, condenser, vent, thermowell, or a combination comprising at least one of the foregoing. The feed stream can be passed through the reactor and can be contacted with a catalyst within the reactor. The temperature within the reactor can be 160° C. to 250° C., for example 180° C. to 230° C., for example, 200° C. to 210° C. Catalyst activity within the reactor can be increased by decreasing the temperature within the catalytic reactor by less than or equal to 20° C. The pressure within the catalytic reactor can be 500 to 5,000 kiloPascals (kPa), for example, 750 to 3,500 kPa, for example, 1,000 to 2,000 kPa.

The reactor of the present disclosure can include a catalyst. The catalyst can include a metal component. For example, the metal component can include cobalt ions (Co), manganese ions (Mn), silver ions (Ag), thallium ions (Tl), or a combination comprising at least one of the foregoing. For example, the catalyst can include less than or equal to 10% of the metal component. For example, the catalyst can include less than or equal to 2% silver ions. For example, the catalyst can include 100 to 500 parts per million (ppm) silver ions. The catalyst can include bromide ($Br^-$). For example, the catalyst can include less than or equal to 15% bromide ions.

The catalyst of the present process can further include a promoter component. For example, the promoter component can include a metal component including, but not limited to, vanadium (V), cesium (Cs), zirconium (Zr), thallium (Tl), or a combination of at least one of the foregoing. The metal promoter component can be present in an amount of less than or equal to 500 ppm. For example, the promoter component can be present in an amount of 500 ppm. The catalyst can include bromide (Br⁻) as a promoter. For example, the catalyst can include less than or equal to 15% bromide ions. The source of the bromide can be a metal counter ion, hydrogen bromide, or 1-Ethyl-3-methylimidazolium bromide. The catalyst of the present process can be dissolved in a solvent. For example, the catalyst of the present process can be dissolved in acetic acid, water, ionic liquid, or a combination comprising at least one of the foregoing. Various non-limiting catalyst compositions in accordance with the present process are listed in Table 1. Cobalt, manganese, and bromide are measured in percent, while vanadium, cesium, and zirconium as measured in parts per million.

TABLE 1

Catalyst Compositions

| Sample | Co (%) | Mn (%) | Br (%) | Ag (ppm) | V (ppm) | Cs (ppm) | Zr (ppm) |
|---|---|---|---|---|---|---|---|
| 1 | 4.03 | 4.03 | 13.91 | — | — | — | — |
| 2 | 4.01 | 4.04 | 13.91 | 209 | — | — | — |
| 3 | 4.04 | 4.04 | 14.01 | 210 | 485 | — | — |
| 4 | 4.02 | 4.03 | 13.95 | 145 | — | 490 | — |
| 5 | 4.03 | 4.01 | 14.00 | 105 | 239 | — | 249 |
| 6 | 4.00 | 3.99 | 13.99 | 214 | — | — | 251 |
| 7 | 4.02 | 4.01 | 14.04 | 215 | — | 245 | 248 |

Various reactions can occur inside the reactor. An oxidation reaction can occur within the reactor. For example, a liquid phase oxidation reaction can occur within the reactor. For example, the liquid phase oxidation of p-xylene to TPA can occur within the reactor. In the present process, it is possible for less than or equal to 25%, for example, less than or equal to 15%, for example, less than or equal to 10%, for example, less than or equal to 5% of the acetic acid solvent to undergo oxidation. The amount of acetic acid oxidation can be measured by monitoring the levels of an optional acetic acid make-up tank. In addition, the amount of acetic acid oxidation can also be measured through analysis of data from an optional acetic acid dehydration column data.

The catalyst of the present process can achieve greater than or equal to 90% selectivity to TPA during the liquid phase oxidation reaction. Silver can act as an efficient oxidation catalyst for p-xylene oxidation. For example, silver can exhibit desirable heat sink material properties such as metal-metal interactions, metal-bromide interactions, thermal conductivity, and easy recoverability. Silver can absorb an arbitrary amount of heat without significantly changing temperature, and can transfer the absorbed heat to any oxygen present, and therefore activate the di-oxygen molecules in the acetic acid-water system. Unique additive effects can also be achieved through the use of silver. For example, enhanced catalyst activation can be achieved due to a direct interaction of the silver with other metals.

The process of the present disclosure can include a product stream that exits the reactor. For example, the product stream can include TPA. The volumetric flow rate of the product stream can be increased greater than or equal to 3%, for example, greater than or equal to 5%, for example, greater than or equal to 7.5%, for example, greater than or equal to 10% by increasing the volumetric flow rate of the feed stream. For example, the flow rates can be increased while the capacity of the catalytic reactor remains the same. The product stream can include greater than or equal to 95%, for example, greater than or equal to 96%, for example, greater than or equal to 97%, for example, greater than or equal to 98% TPA. The product stream of the present process can also include minimal amounts of impurities, such as 4-carboxybenzaldehyde, p-toluic acid, p-tolualdehyde, benzoic acid, 1,4-benzenedimethanol diacetate, and 4-hydroxymethyl benzoic acid. For example, the product stream can include less than or equal to 50,000 ppm 4-carboxybenzaldehyde, for example, less than or equal to 25,000 ppm 4-carboxybenzaldehyde, for example, less than or equal to 20,000 ppm 4-carboxybenzaldehyde, for example, less than or equal to 15,000 ppm 4-carboxybenzaldehyde, for example, less than or equal to 10,000 ppm 4-carboxybenzaldehyde. For example, the product stream can include less than or equal to 1,000 ppm of p-toluic acid.

After exiting the reactor, the product stream of the present process can be further subjected to a process for producing polyester. For example, the product stream can be further subjected to a process for producing polyethylene terephthalate (PET). Polyester fibers based on TPA and PET can provide easy fabric care, both alone and in blends with natural and other synthetic fibers. Polyester films can be used in audio and video recording tapes, data storage tapes, photographic films, labels and other sheet material requiring both dimensional stability and toughness. PET can be used as a primary container resin for application, such as carbonated beverage bottles, while other polyterephthalates can provide dimensional stability, good heat resistance, and durability for engineering applications. TPA can also be used as a paint carrier. TPA can be used in the pharmaceutical industry as a raw material for certain drugs. In addition to these end uses, TPA based polyesters and polyamides can also be used in hot melt adhesives. TPA is also an important raw material for lower molecular weight saturated polyesters for powder and water-soluble coatings. In the research laboratory, TPA can be used as a component for the synthesis of metal-organic frameworks.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to the FIGURE, this schematic represents a process for producing terephthalic acid by oxidation of p-xylene in accordance with the present disclosure. As illustrated in the FIGURE, a feed stream 10, a catalyst stream 11, and an air stream 14 can enter a reactor 12. Once inside the reactor 12, the feed stream 10, catalyst stream 11, and air stream 14 can be continuously stirred by agitator 13. The feed stream 10, catalyst stream 11, and air stream 14 can react with one another to form product stream 16, which can be further processed. Other additional gases and liquids can exit reactor 12 via a vent 19 and a drain 17 respectively. Condenser 18 can control the temperature within reactor 12 while thermowell 15 can allow for safe reactor temperature measurements. The feed stream 10 can include p-xylene and optionally, acetic acid. The catalyst stream 11 can include a metal component such as cobalt ions, manganese ions, silver ions, or a combination including at least one of the foregoing. The liquid phase oxidation of p-xylene to TPA can occur within the reactor. In the present process, it is possible for less than or equal to 25%, for example, less than or equal to 15%, for example, less than or equal to 10%, for example, less than or equal to 5% of the acetic acid solvent to undergo oxidation. The amount of acetic acid oxidation can be measured by monitoring the levels of an optional acetic acid make-up tank. In addition, the amount of acetic acid oxidation can also be measured through analysis of data from an optional acetic acid dehydration column data.

The following examples are merely illustrative of the device disclosed herein and are not intended to limit the scope hereof.

EXAMPLES

TABLE 2

Material Description

| Component | Description | Source |
|---|---|---|
| Cobalt Acetate | Co $(C_2H_3O_2)_2(H_2O)_4$ ($M_w$ = [249.08] g/mol, PS standards) | SigmaAldrich |
| Manganese Bromide | $MnBr_2$ ($M_w$ = [214.75] g/mol, PS standards) | SigmaAldrich |
| Silver Bromide | AgBr ($M_w$ = [187.77] g/mol, PS standards) | SigmaAldrich |
| Silver Acetate | $AgC_2H_3O_2$ ($M_w$ = [166.91] g/mol, PS standards) | SigmaAldrich |

Example 1

A feed stream and a catalyst solution were mixed under a nitrogen atmosphere and fed to a continuously stirred catalytic reactor. The feed stream comprised p-xylene (30 ml, 0.243 moles) and acetic acid (70 ml, 1.215 moles). The catalyst solution comprised $Co^{2+}$ (0.15 moles), $Mn^{2+}$ (0.15 moles), $Br^-$ (0.56 moles), and $Ag^+$ (<500 ppm). The reactor was pressurized to 1000 kiloPascals (kPa) and the temperature within the reactor was set to 185° C. Once a stable temperature was attained, nitrogen pressure was slowly released and air was introduced into the system. The reaction was conducted at a pressure of 1400 kPa for 2 hours. After 2 hours, the reaction material was cooled and filtered. The solid and the mother liquor were analyzed by high performance liquid chromatography (HPLC) and gas chromatography mass spectrometry (GC/GC-MS) respectively. There was no trace of p-xylene found by the GC analysis, indicating that conversion to TPA was 100%. HPLC results showed a product composition of greater than 97% TPA and less than 3% p-toluic acid and other impurities.

The process disclosed herein includes at least the following embodiments:

Embodiment 1

A process for producing terephthalic acid, comprising: passing a feed stream through a catalytic reactor wherein the feed stream comprises p-xylene; contacting the feed stream with a catalyst within the catalytic reactor to produce an oxidation reaction wherein the catalyst comprises, less than or equal to 10% of a metal component wherein the metal component comprises cobalt ions, manganese ions, or a combination comprising at least one of the foregoing, less than or equal to 15% bromide ions, and less than or equal to 2% silver ions; and producing a product stream comprising terephthalic acid, wherein the product stream exits the catalytic reactor.

Embodiment 2

The process of Claim 1, wherein the feed stream comprises less than or equal to 99 mole % p-xylene.

Embodiment 3

The process of Claim 2, wherein the feed stream comprises less than or equal to 90 mole % p-xylene.

Embodiment 4

The process of any of Claims 1-3, wherein the catalyst further comprises a promoter component wherein the promoter component comprises vanadium, cesium, zirconium, thallium, or a combination of at least one of the foregoing.

Embodiment 5

The process of any of Claims 1-4, wherein the catalyst comprises 100 to 500 parts per million silver ions.

Embodiment 6

The process of any of Claims 1-5, wherein the temperature within the catalytic reactor is 160 to 250° C.

Embodiment 7

The process of Claim 6, wherein the catalyst activity is increased by decreasing the temperature within the catalytic reactor by less than or equal to 20° C. as compared to a catalyst not including silver.

Embodiment 8

The process of any of Claims 1-7, wherein the pressure within the catalytic reactor is 1,000 to 2,000 kiloPascals.

Embodiment 9

The process of any of Claims 1-8, further comprising dissolving the catalyst in acetic acid.

Embodiment 10

The process of Claim 9, wherein less than or equal to 10% of the acetic acid undergoes oxidation.

Embodiment 11

The process of any of Claims 1-10, wherein the volumetric flowrate of the product stream is increased greater than or equal to 10% by increasing the volumetric flowrate of the feed stream, wherein the capacity of the catalytic reactor remains the same.

Embodiment 12

The process of any of Claims 1-11, wherein the product stream comprises greater than or equal to 98% terephthalic acid.

Embodiment 13

The process of any of Claims 1-12, wherein the catalyst achieves greater than or equal to 90% selectivity to terephthalic acid.

Embodiment 14

The process of any of Claims 1-13, wherein the product stream comprises less than or equal to 10,000 parts per million 4-carboxybenzaldehyde.

Embodiment 15

The process of Claim 14, wherein the product stream comprises less than or equal to 1,000 parts per million 4-carboxybenzaldehyde.

Embodiment 16

The process of any of Claims 1-15, wherein the product stream comprises less than or equal to 1,000 parts per million of p-toluic acid.

Embodiment 17

The process of any of Claims 1-16, wherein the product stream is further subjected to a process for producing polyester.

Embodiment 18

The process of any of Claims 1-17, wherein the product stream is further subjected to a process for producing polyethylene terephthalate.

Embodiment 19

The process of any of Claims 1-18, wherein the oxidation reaction is a liquid phase oxidation reaction.

Embodiment 20

The process of any of Claims 1-19, wherein the silver content is 200-500 parts per million.

Embodiment 21

The process of any of Claims 1-20, wherein the catalyst further comprises a metal selected from vanadium, cesium, potassium, thallium, or a combination comprising at least one of the foregoing.

Embodiment 22

The process of Claim 21, wherein the metal is present in an amount of less than or equal to 500 parts per million.

Embodiment 23

The process of Claim 22, wherein the metal is present in an amount of 500 parts per million.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

What is claimed is:

1. A process for producing terephthalic acid, comprising:
   passing a feed stream through a catalytic reactor wherein the feed stream comprises p-xylene;
   contacting the feed stream with a catalyst within the catalytic reactor to produce an oxidation reaction wherein the catalyst comprises,
   greater than 0 to 10 mole % of a metal component, based on the feed stream with the catalyst, wherein the metal component comprises cobalt ions, manganese ions, or a combination comprising at least one of the foregoing,
   greater than 0 to 24.2 mole % bromide ions, based on the feed stream with the catalyst, and
   greater than 0 to 500 parts per million silver ions, based on the feed stream with the catalyst; and
   producing a product stream comprising terephthalic acid, wherein the product stream exits the catalytic reactor.

2. The process of claim 1, wherein the feed stream comprises less than or equal to 99 mole % p-xylene.

3. The process of claim 1, wherein the catalyst further comprises a promoter component wherein the promoter component comprises cesium, thallium, or a combination of at least one of the foregoing.

4. The process of claim 1, wherein the catalyst further comprises a promoter component wherein the promoter component comprises vanadium, zirconium, or a combination of at least one of the foregoing.

5. The process of claim 1, wherein the temperature within the catalytic reactor is 160 to 250° C.

6. The process of claim 1, wherein the feed stream comprises less than or equal to 90 mole % p-xylene.

7. The process of claim 1, wherein the pressure within the catalytic reactor is 1,000 to 2,000 kiloPascals.

8. The process of claim 1, further comprising dissolving the catalyst in acetic acid.

9. The process of claim 8, wherein less than or equal to 10 mole % of the acetic acid, based on the feed stream with the catalyst and acetic acid, undergoes oxidation.

10. The process of claim 1, wherein the volumetric flowrate of the product stream is increased greater than or equal to 10% by increasing the volumetric flowrate of the feed stream, wherein the capacity of the catalytic reactor remains the same.

11. The process of claim 1, wherein the product stream comprises greater than or equal to 98 mole % terephthalic acid.

12. The process of claim 1, wherein the catalyst achieves greater than or equal to 90% selectivity to terephthalic acid.

13. The process of claim 1, wherein the product stream comprises less than or equal to 10,000 parts per million 4-carboxybenzaldehyde.

14. The process of claim 13, wherein the product stream comprises less than or equal to 1,000 parts per million 4-carboxybenzaldehyde.

15. The process of claim 1, wherein the product stream comprises less than or equal to 1,000 parts per million of p-toluic acid.

16. The process of claim 1, wherein the product stream is further subjected to a process for producing polyester.

17. The process of claim 1, wherein the oxidation reaction is a liquid phase oxidation reaction.

18. The process of claim 1, wherein the silver content is 100-500 parts per million, based on the feed stream with the catalyst.

19. The process of claim 1, wherein the catalyst further comprises potassium.

20. The process of claim 3, wherein the promoter component is present in an amount of greater than 0 to 500 parts per million, based on the feed stream with the catalyst.

* * * * *